(12) United States Patent
Sullivan et al.

(10) Patent No.: US 11,123,207 B2
(45) Date of Patent: Sep. 21, 2021

(54) STENT DELIVERY SYSTEM

(71) Applicant: Micro Medical Solutions, Inc., Wilmington, MA (US)

(72) Inventors: Gregory Sullivan, Wilmington, MA (US); Benedict Shia, Wilmington, MA (US)

(73) Assignee: Micro Medical Solutions, Inc., Wilmington, MA (US)

( * ) Notice: Subject to any disclaimer, the term of this patent is extended or adjusted under 35 U.S.C. 154(b) by 49 days.

(21) Appl. No.: 15/569,809

(22) PCT Filed: Apr. 29, 2016

(86) PCT No.: PCT/US2016/030180
§ 371 (c)(1),
(2) Date: Oct. 27, 2017

(87) PCT Pub. No.: WO2016/176602
PCT Pub. Date: Nov. 3, 2016

(65) Prior Publication Data
US 2018/0140446 A1    May 24, 2018

Related U.S. Application Data

(60) Provisional application No. 62/154,316, filed on Apr. 29, 2015, provisional application No. 62/165,914, (Continued)

(51) Int. Cl.
*A61F 2/966* (2013.01)
*A61B 17/221* (2006.01)
(Continued)

(52) U.S. Cl.
CPC ............ *A61F 2/966* (2013.01); *A61B 17/221* (2013.01); *A61F 2/95* (2013.01);
(Continued)

(58) Field of Classification Search
CPC .... A61F 2/966; A61F 2/95; A61F 2250/0098; A61F 2002/9528; A61F 2002/9665;
(Continued)

(56) References Cited

U.S. PATENT DOCUMENTS 6,136,006 A     10/2000  Johnson et al.
2002/0052642 A1*  5/2002  Cox ........................ A61F 2/91
                                                          623/1.12
(Continued)

OTHER PUBLICATIONS

International Search Report.
Written Opinion of the International Searching Authority.

*Primary Examiner* — Richard G Louis
(74) *Attorney, Agent, or Firm* — Bay State IP, LLC

(57) ABSTRACT

A stent delivery system, which includes a catheter and a stent stabilizer and pusher mechanism to capture and deploy a braided stent. The stabilizer pusher mechanism has a reinforced polymer shaft with two ends, a hub, a marker band and a braided mesh sock. The stent stabilizer and pusher mechanism further possesses a reinforced polymer shaft, which is constructed to have a low friction lumen. The low friction lumen may be guide wire compatible.

18 Claims, 4 Drawing Sheets

Related U.S. Application Data filed on May 23, 2015, provisional application No. 62/253,839, filed on Nov. 11, 2015.

(51) Int. Cl.
*A61F 2/95* (2013.01)
*A61B 17/22* (2006.01)

(52) U.S. Cl.
CPC .......... *A61B 2017/2215* (2013.01); *A61B 2017/22035* (2013.01); *A61F 2002/9528* (2013.01); *A61F 2002/9665* (2013.01); *A61F 2250/0096* (2013.01); *A61F 2250/0098* (2013.01)

(58) Field of Classification Search
CPC ...... A61F 2250/0096; A61F 2002/9534; A61F 2/9525; A61B 17/221; A61B 2017/2215; A61B 2017/22035
See application file for complete search history.

(56) References Cited

U.S. PATENT DOCUMENTS

| | | |
|---|---|---|
| 2003/0212451 A1 | 11/2003 | Cox et al. |
| 2004/0181237 A1* | 9/2004 | Forde .................. A61F 2/95 606/108 |
| 2007/0055339 A1 | 3/2007 | George et al. |
| 2007/0270932 A1* | 11/2007 | Headley ............... A61F 2/9525 623/1.11 |
| 2010/0100167 A1 | 4/2010 | Bortlein et al. |

* cited by examiner

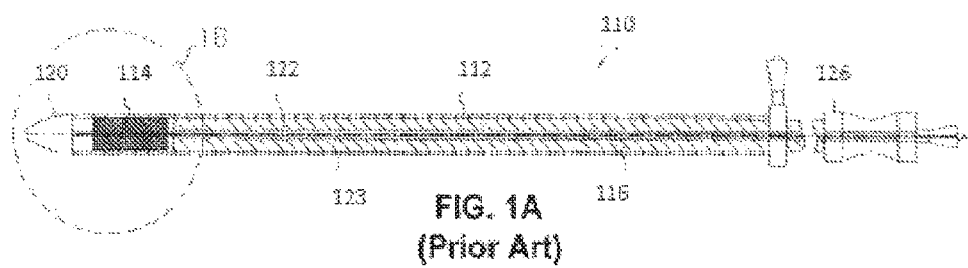
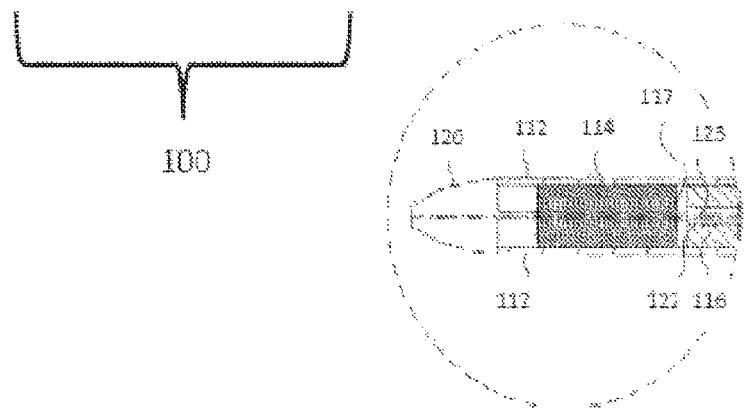
FIG. 1A
(Prior Art)
FIG. 1B
(Prior Art)

STENT DELIVERY SYSTEM

CROSS REFERENCE TO RELATED APPLICATION

This application is for entry into the U.S. National Phase under § 371 for International Application No. PCT/US2016/030180 having an international filing date of Apr. 29, 2016, and from which priority is claimed under all applicable sections of Title of the United States Code including, but not limited to, Sections 120, 363, and 365(c), and which in turn claims priority under 35 USC 119 to U.S. Provisional Patent Application No. 62/154,316 filed on Apr. 29, 2015, U.S. Provisional Patent Application No. 62/165,914 filed on May 23, 2015 and U.S. Provisional Patent Application No. 62/253,839 filed on Nov. 11, 2015.

BACKGROUND OF THE INVENTION

Field of the Invention

The instant system relates generally to medical devices, including surgical and medical delivery systems. More particularly, the instant system relates to stents, catheters, and stent stabilizer and pusher mechanisms.

Description of the Related Art

Within the art, currently disposed stent devices include, but are not limited to, elongated devices used in many capacities, including but not limited to support an intraluminal wall. Stenosis is an abnormal narrowing in a blood vessel or other tubular organ or structure. This vessel narrowing prevents the valve from opening fully, which obstructs blood flow from the heart and onward to the rest of the body.

There concurrently exist a wide variety of stents used for different purposes depending on the type of narrowing of a vessel in the body required. As used herein, the term "stent" is a shorthand reference referring to the wide varieties of stents, both covered and uncovered.

Stents are typically implanted within the vascular system to reinforce collapsing, partially occluded, weakened or under dilated sections of vessel and valves. Stents have also been successfully implanted in urinary tracts and bile ducts to reinforce those body vessels. This invention is applicable in all of these situations.

In general, the typical procedure for implanting a self-expanding stent is to first open the region of the vessel with a balloon catheter and then place the stent in a position bridging the weakened portion of the vessel. Positioning of the stent may be followed by the technique known as the "Swiss Kiss" in which a separate balloon catheter is positioned within the stent and expanded to radially expand the stent for implantation.

SUMMARY OF THE INVENTION

The instant apparatus and system, as illustrated herein, is clearly not anticipated, rendered obvious, or even present in any of the prior art mechanisms, either alone or in any combination thereof. A versatile system, method and series of apparatuses for creating and utilizing a stent stabilizer and pusher mechanism as part of a stent delivery device and other like systems is disclosed.

The present system pertains to improved medical devices providing enhanced precision, strength and utilization properties. Accordingly, an illustrative but non-limiting example of the present system may be found in a medical device such as a stent delivery system that is designed to work in conjunction with s Micro Medical Solutions™, device, which in one system features a (3) French (common abbreviations include: F, Fg, Ga, FR, CH or Ch) stent and delivery system.

In accordance with this invention, there is provided a stent delivery system comprising a stent stabilizer and pusher mechanism, which is designed to be an integral portion of the Micro Medical Solutions™ 3F stent and delivery system.

The stent delivery system comprises a stent, a guidewire lumen, a hub, a marker band, a stabilizer and pusher shaft, and a braided mesh sock attached to the outer diameter of the stabilizer and pusher shaft and also engaged to the stent.

The stent stabilizer and pusher mechanism further comprises a reinforced polymer shaft, which is constructed to have a low friction lumen. The low friction lumen may be guide wire compatible. At the proximal end of the shaft ("proximal" meaning closer to an entry location outside the body), a hub may also be disclosed. At the distal end of the shaft, there is a braided mesh sock, which is constrained at one end beneath a marker band on the outer diameter of the reinforced shaft. The marker band provides a visual reference for a medical staff user when the stent has been released from the 3F guide delivery system and the sock no longer has the stent constrained.

The unconstrained end of the braided sock hangs over the distal end of the shaft and has an unconstrained diameter, which is slightly larger than the diameter of the stent it will capture. The stent is held butted against the inside of the sock (See FIG. 2). As the stent stabilizer and pusher mechanism is pulled back inside the 3F sheath, the sock collapses capturing the stent (See FIG. 3).

In addition, the shaft may comprise any number of polymeric materials and may have any reinforcement material, coil or braid, which will provide sufficient shaft column support as the stent is being advanced or retracted inside the 3F Guide.

Furthermore, the mesh sock may comprise any braiding configuration or material. The sock needs to be able to collapse uniformly and offer sufficient securement of the stent as it is being loaded inside the 3F guide. Any number of wires and/or diameters of wires may be used to construct the sock, as long as it does not inhibit loading the stent or contribute to higher friction as the stent stabilizer and pusher design mechanism is advanced or retraced inside the 3F Guide lumen.

BRIEF DESCRIPTION OF THE DRAWINGS

FIGS. 1A and 1B are longitudinal section illustrations of a stent delivery system of concurrent art, and an enlarged portion thereof;

DETAILED DESCRIPTION OF THE SEVERAL EMBODIMENTS

Figure 2:
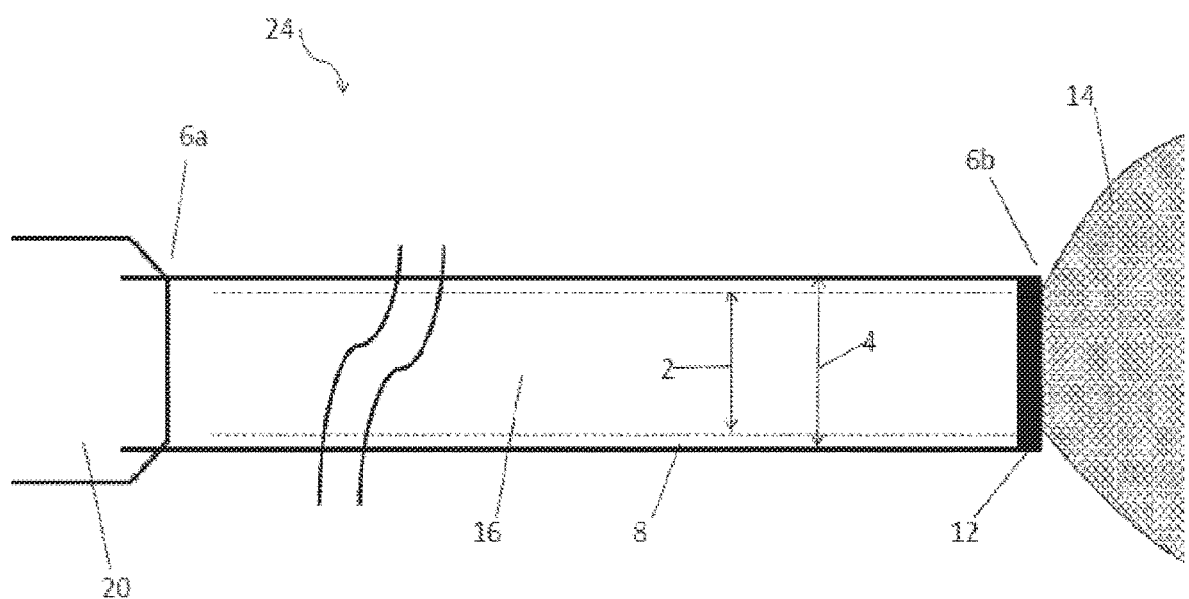
FIG. 2 is a side view partial cross-section illustration of a stent delivery system according to the present invention, depicting the stent stabilizer and pusher mechanism.

For the following defined terms, these definitions shall be applied, unless a different definition is given in the claims or elsewhere in this specification. All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed system.

A typical prior art stent placement mechanism is shown in FIGS. 1A-1B. FIGS. 1A-1B shows a strand pre-loaded stent delivery system 100 comprising an outer sheath 112, a compressed stent 114 loaded therein, and a conventional stabilizer 116 loaded adjacent to the proximal end 117 of the stent. "Proximal" end refers to the end closer to an entry location outside the body. "Distal" end refers to the farthest end from the entry location. The term "stabilizer" is used in the art to describe component 116 of stent delivery systems used to stabilize or prevent retraction of stent 114 when sheath 112 is retracted, thus effecting deployment of the stent into a desired location. The stabilizer 116 limits the movement between the sheath and the stent in order to provide accurate and precise placement.

FIGS. 1A-1B also depict the delivery system 110 comprising a catheter tip 120 as its distal end, which is attached to an internal sheath 123 that runs through the delivery system through the inner lumen 122 in stabilizer 116. A stabilizer handle 126 is typically located at the proximal end of the stabilizer 116, outside the body lumen.

To position and deploy the stent 114, delivery system 10 is directed through the body lumen to the patient's desired and needed location for stent deployment and vessel repair. Outer sheath 112 is then retracted, and stabilizer 116 acts as a stabilizer to keep stent 114 from retracting with the sheath. As outer sheath 112 retracts, stent 114 is exposed and expands into place in the patient's body.

Figure 3:
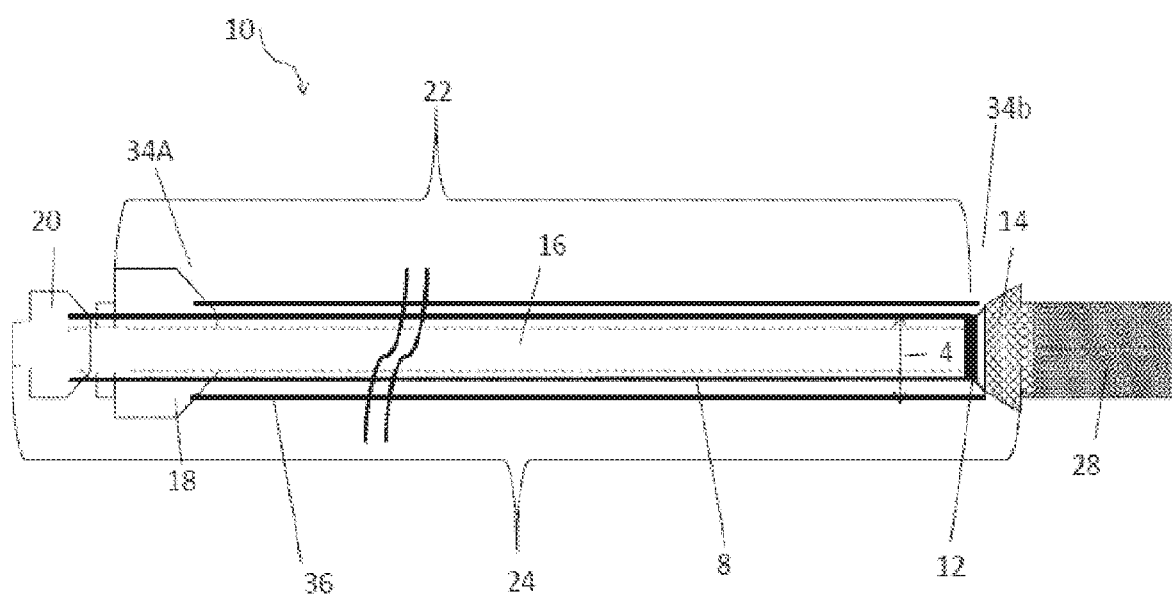
FIG. 3 is a side view partial cross-section illustration of a stent delivery system according to the present invention depicting the stent stabilizer and pusher mechanism engaging the braided stent; and, FIG. 4 is a side view partial cross-section illustration of a stent delivery system according to the present invention depicting the loading of the stent inside the 3F Guide using the stent stabilizer and pusher mechanism.

FIG. 2 illustrates one embodiment for a stent stabilizer and pusher mechanism 24 that may be utilized in conjunction with and as a stent delivery system 10 (see FIG. 3). In one embodiment, the stent stabilizer and pusher mechanism 24 comprises a reinforced polymer shaft 8, wherein the polymer shaft 8 may be constructed to have low friction. The polymer shaft 8 further comprises a lumen 16; in one embodiment the low friction lumen 16 may be guide wire compatible. The polymer shaft 8 further comprises a proximal end 6A and a distal end 6B, wherein the proximal end 6A may be defined as meaning closer to an entry location outside the body. In one embodiment, a pusher hub 20 is positioned at the proximal end 6A of the shaft 8, and a braided mesh sock 14 is positioned at the distal end 6B of the shaft 8. In a preferred embodiment, the braided mesh sock 14 may be constructed with 36 strands of 0.001" nickel titanium. Furthermore, in another embodiment, the braided mesh sock 14 would comprise a construction of one over braid and one under braid with a braid angle at approximately one hundred twenty degrees. In separate embodiments, the braid configuration and braid material for the braided mesh sock 14 may comprise any braid and material, which may successfully capture and pull a stent inside a corresponding guide wire. In one embodiment, the braided mesh sock 14 is constrained at the distal end 6B of the shaft 8 beneath a marker band 12.

Additionally, the shaft 8 comprises an inner diameter 2 and an outer diameter 4, wherein the inner diameter 2 of the shaft is approximately 0.021" and the outer diameter 4 of the shaft is approximately 0.030". Furthermore, the mesh sock 14 includes a diameter which is a heat set diameter and is approximately 0.5 mm. In one embodiment, it is preferable that the heat set diameter be approximately 0.5-1.0 mm larger than the stent captured by the braided mesh sock 14.

FIG. 3 illustrates a side-view partial cross-sectional of the stent delivery system 10 showing the stent stabilizer and pusher mechanism 24 engaging a braided stent 28 and located within a catheter 22. In this embodiment, the catheter 22 comprises a polymer shaft 36 with a proximal end 34A and a distal end 34B.

In this embodiment, the braided mesh sock 14 is attached to the outer diameter 4 of the stent stabilizer and pusher mechanism 24, within the catheter 22. Furthermore, the braided mesh sock 14 is bonded to the marker band 12, and the bond is terminated beneath the marker band 12.

Additionally, the braided mesh sock 14 is also engaged with the braided stent 28. In one embodiment, the stabilizer and pusher mechanism 24 may accept a guide wire (not shown) through the lumen 16, which assists with the tracking of the stent delivery system 10. At the proximal end 34A of the catheter 22 there may be a catheter hub 18.

Figure 4:
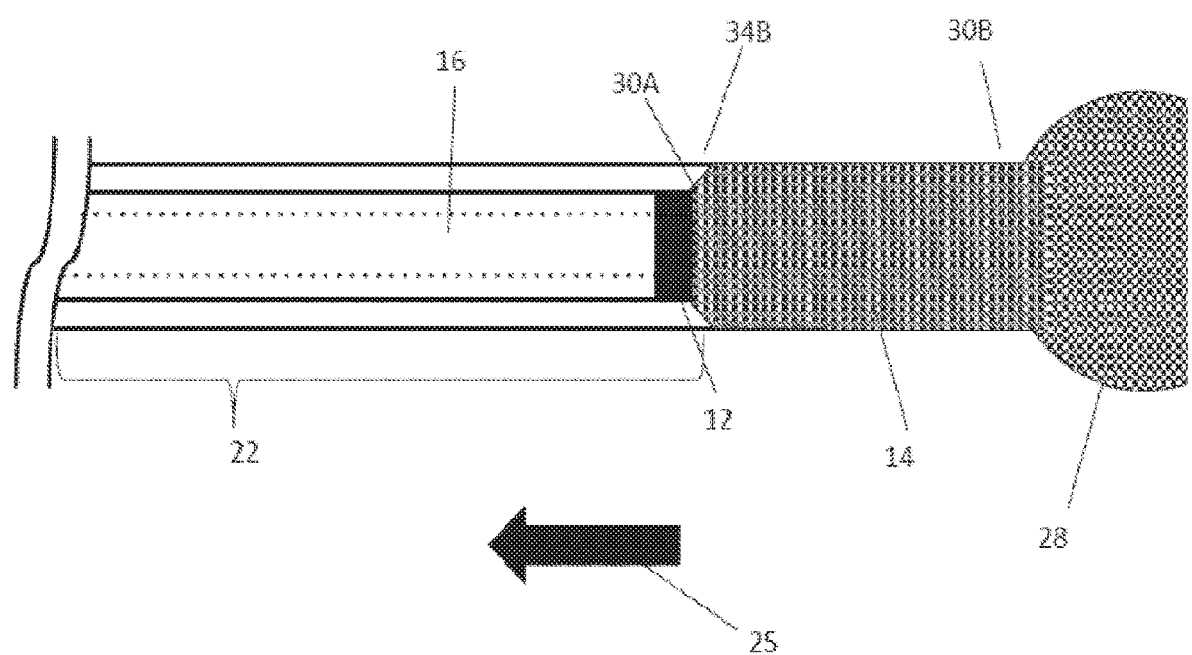

FIG. 4 illustrates a side view partial cross-section of the stent delivery system 10 showing the loading of the braided stent 28 inside the 3 French ("3F") catheter 22 using the stent stabilizer and pusher mechanism 24.

At the distal end 34B of the catheter 22 the braided mesh sock 14 is collapsed and secured around the braided stent 28. In one embodiment, the stent mechanism 28 is held butted against an inside of the mesh sock 14. As seen, the mesh sock comprises a constrained end 30A and an unconstrained end 30B. Further, the retraction of the stent stabilizer and pusher mechanism 24 pulls the braided stent 28 inside the catheter 22 toward the hub 18 as depicted by a directional arrow 25. In this embodiment the braided stent 28 is pulled toward the proximal end 34A of the catheter 22.

In conclusion, herein is presented a stent delivery system utilizing a stent stabilizer and pusher mechanism. The system is illustrated by example in the drawing figures, and throughout the written description. It should be understood that numerous variations are possible, while adhering to the inventive concept. Such variations are contemplated as being a part of the present system.

What is claimed is:

1. A stent delivery system comprising:
   a catheter, wherein the catheter further comprises:
   a polymer shaft, wherein the shaft comprises a proximal end and a distal end; and
   a catheter hub;
   a stent stabilizer and pusher mechanism located within the catheter, wherein the stent stabilizer and pusher mechanism further comprises:
   a reinforced polymer shaft, wherein the polymer shaft comprises a proximal end and a distal end;

a pusher hub, wherein the pusher hub is attached to the proximal end of the reinforced polymer shaft of the stent stabilizer and pusher mechanism;

a marker band; and a braided mesh sock, wherein the braided mesh sock is bonded to the marker band and the bond is terminated beneath the marker band, further comprises:

a constrained end by which the constrained end is attached to the distal end of the reinforced polymer shaft underneath the marker band;

an unconstrained end; and a free diameter from which the braided mesh sock is collapsed on drawing inside the polymer shaft of the catheter; and a stent, wherein a proximal end of the stent is engaged by the braided mesh sock, the braided mesh sock being collapsed onto the stent and the stent being held butted against an inside of the braided mesh sock, whereby the stent is drawn into the catheter and secured therein;

wherein the marker band provides a visual reference when the stent has been released from the delivery system and the braided mesh sock no longer has the stent constrained.

2. The stent delivery system of claim 1, wherein reinforced polymer shaft of the stent stabilizer and pusher mechanism further comprises a low friction lumen.

3. The stent delivery system of claim 2, wherein the low friction lumen is guide wire compatible.

4. The stent delivery system of claim 1, wherein the stent mechanism is held butted against an inside of the mesh sock.

5. The stent delivery system of claim 1, wherein the braided sock hangs over the distal end of the reinforced polymer shaft.

6. The stent delivery system of claim 1, wherein the braided mesh sock comprises a configuration of braiding wires.

7. The stent delivery system of claim 6, wherein the configuration of braiding wires comprises a set of strands.

8. The stent delivery system of claim 7, wherein the configuration of braiding wires is constructed of a set of 36 strands.

9. The stent delivery system of claim 8, wherein the set of 36 strands comprise a diameter of 0.001".

10. The stent delivery system of claim 8, wherein the set of 36 strands comprise nickel titanium.

11. The stent delivery system of claim 7, wherein the set of strands comprises at least one over braid and at least one under braid.

12. The stent delivery system of claim 7, wherein the set of strands comprises at least one over braid and at least one under braid and wherein the at least one over braid and the at least one under braid comprises a braid angle of 120 degrees.

13. The stent delivery system of claim 2, wherein the inner diameter of the low friction lumen is 0.021".

14. The stent delivery system of claim 2, wherein the outer diameter of the lumen is about 0.030".

15. The stent delivery system of claim 1, wherein the diameter of the mesh sock is 0.5 mm.

16. The stent delivery system of claim 1 wherein the diameter of the mesh sock comprises a heat set diameter.

17. The stent delivery system of claim 16, wherein the heat set diameter is a range of 0.5-1.0 mm larger than the stent to be captured.

18. The stent delivery system of claim 1, wherein the braided mesh sock is collapsible and secures the stent.

* * * * *